(12) United States Patent
Cai et al.

(10) Patent No.: US 6,528,649 B2
(45) Date of Patent: Mar. 4, 2003

(54) IMIDAZOLOISOQUINOLINES

(75) Inventors: Guolin Cai, Thousand Oaks, CA (US); Kenneth Shaw, Weston, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/867,304

(22) Filed: May 29, 2001

(65) Prior Publication Data

US 2002/0019410 A1 Feb. 14, 2002

Related U.S. Application Data

(60) Provisional application No. 60/207,796, filed on May 30, 2000.

(51) Int. Cl.$^7$ .................. C07D 471/04; A61K 31/437; A61P 25/00
(52) U.S. Cl. .............. 546/84; 546/86; 546/87; 544/234; 544/333; 544/405; 514/292; 514/248; 514/255.05; 514/256
(58) Field of Search ................ 546/84; 544/234, 544/333, 405; 514/256, 292, 248, 255.05

(56) References Cited

U.S. PATENT DOCUMENTS

| | | | | |
|---|---|---|---|---|
| 5,608,079 A | * | 3/1997 | Albaugh | 548/492 |
| 6,159,985 A | * | 12/2000 | Liu | 514/292 |

FOREIGN PATENT DOCUMENTS

| | | |
|---|---|---|
| EP | 0 290 153 A | 11/1988 |
| EP | 0 581 960 A | 2/1994 |
| EP | 0 650 960 A | 5/1995 |
| EP | 0 911 340 A | 5/1999 |
| WO | WO 98/50385 | 11/1998 |
| WO | WO 00/29412 | 5/2000 |

OTHER PUBLICATIONS

ACH–Models Chem. (1998), 135(4), 439–447.
J. Org. Chem. (1995), 60(5), 1466–9.
Iyo kizai Kenkyusho Hokoku (Tokyo Ila Shika Daigaku) (1992), 26, 85–6.
Iyo kizai Kenkyusho Hokoku (Tokyo Ila Shika Daigaku) (1990), 24, 41–8.

* cited by examiner

Primary Examiner—Evelyn Mei Huang
(74) Attorney, Agent, or Firm—McDonnell Boehnen Hulbert & Berghoff

(57) ABSTRACT

Disclosed are compounds of the formula:

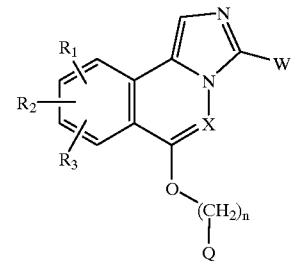

and the pharmaceutically acceptable salts, prodrugs and solvates thereof, wherein n, $R_1$, $R_2$, $R_3$, W, Q, and X are defined herein, which compounds bind with high selectivity and high affinity to the benzodiazepine site of the $GABA_A$ receptors and are therefore useful in the treatment of certain central nervous system (CNS) diseases and as probes for the localization of $GABA_A$ receptors in tissue samples.

26 Claims, No Drawings

IMIDAZOLOISOQUINOLINES

This application claims priority from U.S. Provisional Application Ser. No. 60/207,796, filed May 30, 2000, the disclosure of which is incorporated herein in its entirety.

BACKGROUND OF THE INVENTION

1. Field of the Invention

This invention relates to imdazoloisoquinolines and more specifically to such compounds that bind with high selectivity and high affinity to the benzodiazepine site of $GABA_A$ receptors. This invention also relates to pharmaceutical compositions comprising such compounds and to the use of such compounds in treatment of certain central nervous system (CNS) diseases.

2. Description of the Related Art

The $GABA_A$ receptor superfamily represents one of the classes of receptors through which the major inhibitory neurotransmitter, γ-aminobutyric acid, or GABA, acts. Widely, although unequally, distributed through the mammalian brain, GABA mediates many of its actions through a complex of proteins called the $GABA_A$ receptor, which causes alteration in chloride conductance and membrane polarization.

A number of cDNAs for $GABA_A$ receptor subunits have been characterized. To date at least 6α, 3β, 3γ, 1ε, 1δ and 2ρ subunits have been identified. It is generally accepted that native $GABA_A$ receptors are typically composed of 2α, 2β, and 1γ subunits (Pritchett & Seeburg *Science* 1989; 245:1389–1392 and Knight et. al., *Recept. Channels* 1998; 6:1–18). Evidence such as message distribution, genome localization and biochemical study results suggest that the major naturally occurring receptor combinations are $\alpha_1\beta_2\gamma_2$, $\alpha_2\beta_3\gamma_2$, $\alpha_3\beta_3\gamma_2$, and $\alpha_5\beta_3\gamma_2$ (Mohler et. al. *Neuroch. Res.* 1995; 20(5): 631–636).

Benzodiazepines exert their pharmacological actions by interacting with the benzodiazepine binding sites associated with the $GABA_A$ receptor. In addition to the benzodiazepine site, the $GABA_A$ receptor contains sites of interaction for several other classes of drugs. These include a steroid binding site, a picrotoxin site, and the barbiturate site. The benzodiazepine site of the $GABA_A$ receptor is a distinct site on the receptor complex that does not overlap with the site of interaction for GABA or for other classes of drugs that bind to the receptor (see, e.g., Cooper, et al., The Biochemical Basis of Neuropharmacology, $6^{th}$ ed., 1991, pp. 145–148, Oxford University Press, New York). Early electrophysiological studies indicated that a major action of the benzodiazepines was enhancement of GABAergic inhibition. Compounds that selectively bind to the benzodiazepine site and enhance the ability of GABA to open $GABA_A$ receptor channels are agonists of GABA receptors. Other compounds that interact with the same site but negatively modulate the action of GABA are called inverse agonists. Compounds belonging to a third class bind selectively to the benzodiazepine site and yet have little or no effect on GABA activity, but can block the action of $GABA_A$ receptor agonists or inverse agonists that act at this site. These compounds are referred to as antagonists.

The important allosteric modulatory effects of drugs acting at the benzodiazepine site were recognized early and the distribution of activities at different receptor subtypes has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have a long history of pharmaceutical use as anxiolytics, these compounds often exhibit a number of unwanted side effects. These may include cognitive impairment, sedation, ataxia, potentiation of ethanol effects, and a tendency for tolerance and drug dependence.

$GABA_A$ selective ligands may also act to potentiate the effects of certain other CNS active compounds. For example, there is evidence that selective serotonin reuptake inhibitors (SSRIs) may show greater antidepressant activity when used in combination with $GABA_A$ selective ligands than when used alone.

SUMMARY OF THE INVENTION

Disclosed are certain novel compounds, particularly imidazoloisoquinolines that bind to cell surface receptors. Preferred compounds of the invention bind to GABA receptors, in particular these compounds possess affinity for the benzodiazepine site of $GABA_A$ receptors, including human $GABA_A$ receptors. Also preferred are compounds that exhibit high selectivity to the benzodiazepine site of the $GABA_A$ receptor. These compounds are therefore considered to be of potential use in the treatment of a broad array of diseases or disorders in patients, which are characterized by modulation of $GABA_A$ receptors.

Such diseases or disorders include, but are not limited to depression, anxiety, sleep disorders, cognitive disorders, low alertness, psychosis, obesity, pain, Parkinson's disease, Alzheimer's disease, neurodegenerative diseases, movement disorders, Down's syndrome, and benzodiazepine overdoses.

Thus, the invention provides compounds of Formula I (shown below), and pharmaceutical compositions comprising compounds of Formula I.

The invention further comprises methods of treating patients suffering from certain CNS disorders with a therapeutically effective amount of a compound of the invention. The patient may be a human or other mammal. Treatment of humans, domesticated companion animals (pet) or livestock animals suffering from certain CNS disorders with a therapeutically effective amount of a compound of the invention is encompassed by the invention.

In a separate aspect, the invention provides a method of potentiating the actions of other CNS active compounds. This method comprises administering a therapeutically effective amount of a compound of the invention with another CNS active compound.

Additionally this invention relates to the use of the compounds of the invention as probes for the localization of $GABA_A$ receptors in tissue sections.

Accordingly, a broad aspect of the invention is directed to compounds of Formula I:

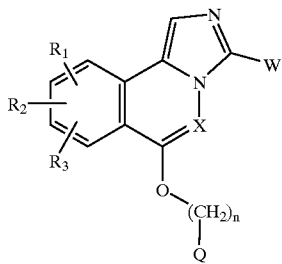

Formula I and the pharmaceutically acceptable salts, prodrug, or solvate thereof, wherein n, $R_1$, $R_2$, $R_3$, W, Q, and X are defined below.

In another aspect, the invention provides intermediates useful for preparing the compounds of Formula I.

In a further aspect, the invention provides methods for making compounds of Formula I.

DETAILED DESCRIPTION OF THE INVENTION

The invention is directed to compounds and pharmaceutically acceptable salts, prodrugs, and solvates of compounds of Formula I (shown above) wherein n is 1, 2, 3, or 4, $R_1$, $R_2$, and $R_3$ are the same or different and represent:

i) hydrogen, halogen, hydroxy, ii) $R_a$ wherein $R_a$ is
—O($C_{1-8}$ alkyl), —$NO_2$, —CN, —$SO_2NH_2$, —$SO_2NH$ ($C_{1-8}$ alkyl), —$SO_2N(C_{1-8}$ alkyl) ($C_{1-8}$ alkyl), amino, —NH($C_{1-8}$ alkyl), —N($C_{1-8}$ alkyl)($C_{1-8}$ alkyl), —NHCO($C_{1-8}$ alkyl),
—N($C_{1-8}$ alkyl)CO($C_{1-8}$ alkyl), —NHCO$_2$($C_{1-8}$ alkyl), —N($C_{1-8}$ alkyl)CO$_2$($C_{1-8}$ alkyl), —NHSO$_2$($C_{1-8}$ alkyl), —CONH$_2$, —CONH($C_{1-8}$ alkyl), —CON($C_{1-8}$ alkyl) ($C_{1-8}$ alkyl), —CO$_2$($C_{1-8}$ alkyl), —S($C_{1-8}$ alkyl), —SO($C_{1-8}$ alkyl), or —SO$_2$($C_{1-8}$ alkyl), wherein each $C_{1-8}$ alkyl independently is straight, branched or cyclic, contains zero, one or two double or triple bonds, and is optionally substituted with one or more of hydroxy, oxo, halogen, amino, or $C_{1-8}$ alkoxy, or $R_a$ is $C_{1-8}$ alkyl, which is straight, branched or cyclic, contains zero, one or two double or triple bonds, and is unsubstituted or substituted with one or more of a) hydroxy, b) oxo, c) halogen, e) —O($C_{1-8}$ alkyl),
f) —NR$_4$R$_5$ wherein
  R$_4$ and R$_5$ are independently selected from hydrogen and $C_{1-8}$ alkyl, or
  R$_4$ and R$_5$ may be joined together to form a monocyclic or bicyclic ring, each of which may contain one or more double bonds, or one or more of oxo, O, S, SO, SO$_2$ or N—R$_6$,
  wherein R$_6$ is hydrogen, $C_{1-6}$ alkyl, $C_{1-6}$ alkyl-Ar$_2$, wherein Ar$_2$ is attached to $C_{1-6}$ alkyl at any position and is optionally substituted with one or two groups, R$_b$ and R$_c$, wherein R$_b$ and R$_c$ independently carry the definition of R$_a$, or
g) —CONR$_7$R$_8$, or —CO$_2$R$_7$ wherein each R$_7$ and R$_8$ is independently hydrogen or $C_{1-6}$ alkyl, iii) Ar$_1$,
wherein Ar$_1$ is phenyl, pyridyl, pyrazinyl, pyrimidinyl, imidazolyl, furanyl, thiazolyl, isothiazolyl, isoxazolyl, oxadiazolyl, triazolyl, tetrazolyl, or pyrazolyl, each of which is unsubstituted or substituted with hydrogen, halogen, hydroxy, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl) ($C_{1-8}$ alkyl), amino, —NH($C_{1-8}$ alkyl), —N($C_{1-8}$ alkyl) ($C_{1-8}$ alkyl), —NHCO($C_{1-8}$ alkyl), —N($C_{1-8}$ alkyl)CO($C_{1-8}$ alkyl), —NHCO$_2$($C_{1-8}$ alkyl), —N($C_{1-8}$ alkyl)CO$_2$($C_{1-8}$ alkyl), —NHSO$_2$ ($C_{1-8}$ alkyl), —CONH$_2$, —CONH($C_{1-8}$ alkyl), —CON ($C_{1-8}$ alkyl) ($C_{1-8}$ alkyl), —CO$_2$($C_{1-8}$ alkyl), —S($C_{1-8}$ alkyl), —SO($C_{1-8}$ alkyl), or —SO$_2$($C_{1-8}$ alkyl), —CONR$_7$R$_8$, or —CO$_2$R$_7$ (wherein each R$_7$ and R$_8$ is independently hydrogen or $C_{1-6}$ alkyl)

wherein each $C_{1-8}$ alkyl independently is straight, branched or cyclic, contains zero, one or two double or triple bonds, and is optionally substituted with one or more of hydroxy, oxo, halogen, amino, or $C_{1-8}$ alkoxy;

X is CR$_d$ or N, wherein R$_d$ carries the same definition as R$_a$;

W is phenyl, naphthyl, thienyl, benzothienyl, pyridyl, isoquinolyl, quinolyl, pyrazinyl, pyrimidinyl, imidazolyl, benzoimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl or benzopyrazolyl, each of which is unsubstituted or substituted with one or more of:

hydrogen, halogen, hydroxy, alkoxy, R$_x$ where R$_x$ carries the same definition as R$_a$, or Ar$_3$ wherein Ar$_3$ carries the same definition as Ar$_1$; and Q is thienyl, benzothienyl, pyridyl, isoquinolyl, quinolyl, pyrazinyl, pyrimidinyl, imidazolyl, benzoimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, benzopyrazolyl, where each of which is unsubstituted or substituted with one or more of:

hydrogen, halogen, hydroxy, alkoxy, R$_y$ where R$_y$ carries the same definition as R$_a$, or Ar$_4$ wherein Ar$_4$ carries the same definition as Ar$_1$.

Preferred compound of Formula I include those compounds where X is CH.

Other preferred compounds and salts of Formula I are those wherein:

or a pharmaceutically acceptable salt thereof, wherein:

n is 1, 2, 3, or 4, $R_1$, $R_2$, and $R_3$ are independently selected from hydrogen, halogen, hydroxy, $C_{1-8}$alkyl, —O($C_{1-8}$ alkyl), —NO$_2$, —CN, -amino, —NH($C_{1-8}$ alkyl), and —N($C_{1-8}$ alkyl) ($C_{1-8}$ alkyl);

X is N, CH or C($C_{1-6}$alkyl);

W is phenyl, thienyl, pyridyl, pyrazinyl, pyrimidinyl, imidazolyl, furanyl, thiazolyl, pyrrolyl, triazolyl, or pyrazolyl;

each of which is unsubstituted or substituted with one to three groups independently selected from halogen, hydroxy, $C_{1-8}$alkyl, —O($C_{1-8}$ alkyl), —NO$_2$, —CN, -amino, —NH($C_{1-8}$ alkyl), and —N($C_{1-8}$ alkyl) ($C_{1-8}$ alkyl); and Q is phenyl, thienyl, pyridyl, pyrazinyl, pyrimidinyl, imidazolyl, furanyl, thiazolyl, pyrrolyl, triazolyl, or pyrazolyl;

each of which is unsubstituted or substituted with one to three groups independently selected from halogen, hydroxy, $C_{1-8}$alkyl, —O($C_{1-8}$ alkyl), —NO$_2$, —CN, -amino, —NH($C_{1-8}$ alkyl), and —N($C_{1-8}$ alkyl) ($C_{1-8}$ alkyl).

In an alternate embodiment the invention includes compounds of Formula II

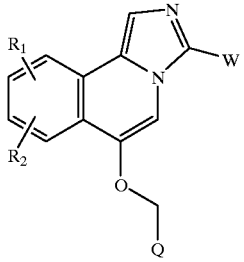

Formula II wherein W, Q, $R_1$ and $R_2$ are as defined for Formula I.

Another embodiment of the invention includes compounds of Formula III

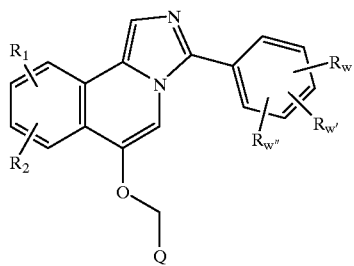

Formula III where $R_w$, $R_w'$, and $R_w''$ independently represent hydrogen, halogen, hydroxy, or $R_z$ wherein $R_z$ carries the same definition as $R_a$ for Formula I.

Particularly preferred compounds of Formula III are those where Q is pyridyl, imidazolyl, thienyl, or phenyl optionally substituted as defined in Formula I.

Other preferred compounds of Formula III are those wherein $R_1$, $R_2$, independently selected from hydrogen, halogen, hydroxy, $C_{1-8}$alkyl, —O($C_{1-8}$ alkyl), —$NO_2$, —CN, -amino, —NH($C_{1-8}$ alkyl), and —N($C_{1-8}$ alkyl) ($C_{1-8}$ alkyl);

Q is phenyl, thienyl, pyridyl, pyrazinyl, pyrimidinyl, imidazolyl, furanyl, thiazolyl, pyrrolyl, triazolyl, or pyrazolyl;
each of which is unsubstituted or substituted with one to three groups independently selected from halogen, hydroxy, $C_{1-8}$alkyl, —O($C_{1-8}$ alkyl), —$NO_2$, —CN, -amino, —NH($C_{1-8}$ alkyl), and —N($C_{1-8}$ alkyl) ($C_{1-8}$ alkyl); and $R_w$, $R_w'$, and $R_w''$ are independently chosen from hydrogen, halogen, hydroxy, $C_{1-4}$alkyl, —O($C_{1-4}$ alkyl), —$NO_2$, —CN, -amino, —NH($C_{1-4}$ alkyl), and —N($C_{1-4}$ alkyl) ($C_{1-4}$ alkyl).

The invention also encompasses compounds of Formula IV:

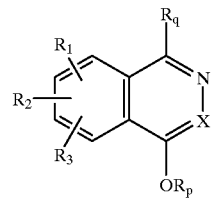

IV wherein
X, $R_1$, $R_2$, and $R_3$ carry the same definitions as given above for Formula I;
$R_p$ is hydrogen, $C_1$–$C_6$ alkyl, or phenyl($C_1$–$C_6$)alkyl; and
$R_q$ is halogen, cyano, aminomethyl, or mono- or di($C_1$–$C_6$)alkylamino.

Preferred compounds of Formula IV include those where $R_p$ is hydrogen or benzyl. Particular compounds of Formula IV are those where $R_p$ is hydrogen, and $R_q$ is halogen or aminomethyl. Other preferred compounds of Formula IV include those where $R_p$ is benzyl; and $R_q$ is halogen or cyano. Particularly preferred compounds of Formula IV include those where $R_p$ is benzyl and $R_q$ is chloro, bromo, or cyano.

Another preferred group of compounds of Formula IV include those where X is CH, and $R_p$ is hydrogen or benzyl. Particular compounds of Formula IV are those where X is CH, $R_p$ is hydrogen, and $R_q$ is halogen or aminomethyl. Other preferred compounds of Formula IV include those where X is CH, $R_p$ is benzyl; and $R_q$ is halogen or cyano. Particularly preferred compounds of Formula IV include those where X is CH, $R_p$ is benzyl and $R_q$ is chloro, bromo, or cyano.

Preferred compounds of Formula IV include those where $R_1$, $R_2$, and $R_3$ independently represent hydrogen, halogen, hydroxy, amino, or mono- or di($C_1$–$C_6$)alkylamino, $C_1$–$C_6$ alkyl, or $C_1$–$C_6$ alkoxy. Particularly preferred $R_1$, $R_2$, and $R_3$ groups are hydrogen, halogen, hydroxy, $C_1$–$C_2$ alkoxy, and $C_1$–$C_2$ alkyl.

The invention also encompasses compounds of Formula V

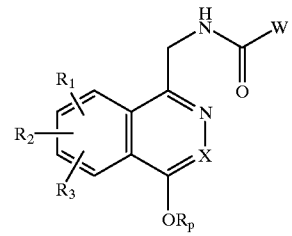

V where
X, W, $R_1$, $R_2$, and $R_3$ carry the same definitions as given above for Formula I; and
$R_p$ is hydrogen, $C_1$–$C_6$ alkyl, or phenyl($C_1$–$C_6$)alkyl.

Preferred compounds of Formula V include those where $R_1$, $R_2$, and $R_3$ independently represent hydrogen, halogen, hydroxy, amino, or mono- or di($C_1$–$C_6$)alkylamino, $C_1$–$C_6$ alkyl, or $C_1$–$C_6$ alkoxy. Particularly preferred $R_1$, $R_2$, and $R_3$ groups are hydrogen, halogen, hydroxy, $C_1$–$C_2$ alkoxy, and $C_1$–$C_2$ alkyl.

Other preferred compounds of Formula V include those where $R_p$ is hydrogen or benzyl. Particular compounds of Formula IV are those where $R_p$ is hydrogen and W is optionally substituted phenyl. Other preferred compounds of Formula IV include those where $R_p$ is benzyl.

Another preferred group of compounds of Formula IV include those where X is CH, and $R_p$ is hydrogen or benzyl. Particular compounds of Formula IV are those where X is CH, $R_p$ is hydrogen, and W is optionally substituted phenyl.

The invention also encompasses compounds of Formula VI

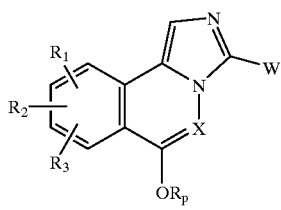

VI where W, $R_1$, $R_2$, and $R_3$ carry the same definitions as given above for Formula I, and $R_p$ is as defined for Formula VI.

Preferred compounds of Formula I include those where X is CH and W is optionally substituted phenyl. Further preferred compounds of Formula VI include those where $R_1$, $R_2$, and $R_3$ independently represent hydrogen, halogen, hydroxy, amino, or mono- or di($C_1$–$C_6$)alkylamino, $C_1$–$C_6$ alkyl, or $C_1$–$C_6$ alkoxy. Particularly preferred compounds of Formula VI include those where $R_p$ is hydrogen.

The following numbering system is used when describing the compounds of the invention:

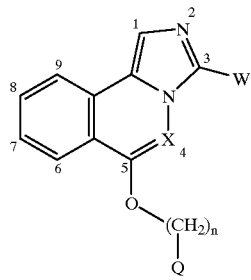

If the compounds of the present invention have asymmetric centers, then this invention includes all of the optical isomers and mixtures thereof.

In addition, compounds with carbon-carbon double bonds may occur in Z- and E- forms, with all isomeric forms of the compounds being included in the present invention.

Included in the invention are non-toxic pharmaceutically acceptable salts of compounds of general Formula I, II, III and the compounds disclosed in the examples which follow. Non-toxic pharmaceutically acceptable salts include, but are not limited to salts with inorganic acids such as hydrochloride, sulfate, phosphate, diphosphate, hydrobromide, and nitrite or salts with an organic acid such as malate, maleate, fumarate, tartrate, succinate, citrate, acetate, lactate, methanesulfonate, p-toluenesulfonate, 2-hydroxyethylsulfonate, salicylate and stearate. Similarly, pharmaceutically acceptable cations include, but are not limited to sodium, potassium, calcium, aluminum, lithium and ammonium.

The present invention also encompasses the prodrugs of the compounds of Formula I. Those skilled in the art will recognize various synthetic methodologies that may be employed to prepare non-toxic pharmaceutically acceptable prodrugs of the compounds encompassed by Formula I.

Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

When any variable (e.g. $C_{1-6}$ alkyl, $C_{1-8}$ alkyl, $R_1$–$R_8$, W, X, $R_1$, $R_2$, $R_3$ or Q) occurs more than one time in Formula I, its definition on each occurrence is independent of its definition at every other occurrence.

This invention relates to heterocyclic derivatives that bind with high affinity and high selectivity to the benzodiazepine site of $GABA_A$ receptors, including human $GABA_A$ receptors.

The invention also provides pharmaceutical compositions comprising compounds of the invention.

The invention further comprises methods of treating patients in need of such treatment with an amount of a compound of the invention sufficient to alter the symptoms of a CNS disorder.

The diseases and/or disorders that can be treated using compounds and compositions of the invention include:

Depression: depression, atypical depression, bipolar disorder, depressed phase of bipolar disorder.

Anxiety: general anxiety disorder (GAD), agoraphobia, panic disorder +/−agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclopthymia Sleep Disorders: sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder Cognition impairment: cognition impairment, Alzheimer's disease, Parkinson's disease, mild cognitive impairment (MCI) age-related cognitive decline (ARCD), stroke, traumatic brain injury, AIDS associate dementia, dementia associated with depression, anxiety or psychosis.

Compounds of the inventions that act as agonists at $\alpha_2\beta_3\gamma_2$ and $\alpha_3\beta_3\gamma_2$ receptor subtypes are useful in treating anxiety disorders such as panic disorder, obsessive compulsive disorder and generalized anxiety disorder; stress disorders including post-traumatic stress, and acute stress disorders. Compounds of the inventions that act as agonists at $\alpha_2\beta_3\gamma_2$ and $\alpha_3\beta_3\gamma_2$ receptor subtypes are also useful in treating depressive or bipolar disorders and in treating sleep disorders. Compounds of the invention that act as inverse agonists at the $\alpha_5\beta_3\gamma_2$ receptor subtype or $\alpha_1\beta_2\gamma_2$ and $\alpha_5\beta_3\gamma_2$ receptor subtypes are useful in treating cognitive disorders including those resulting from Down Syndrome, neurodegenerative diseases such as Alzheimer's disease and Parkinson's disease, and stroke related dementia. Compounds of the invention that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

In a separate aspect, the invention provides a method of potentiating the actions of other CNS active compounds, which comprises administering a therapeutically effective amount of a compound of the invention in combination with another CNS active compound. Such CNS active compounds include, but are not limited to the following: for anxiety, serotonin receptor (e.g. 5-$HT_{1A}$) agonists and antagonists; for anxiety and depression, neurokinin receptor antagonists or corticotropin releasing factor receptor (CRF$_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Particularly the invention provides a method of potentiating the antidepressant activity of selective serotonin reuptake inhibitors (SSRIs) by administering a therapeutically effective amount of a GABA agonist compound of the invention in combination with an SSRI.

Combination administration can be carried out in a fashion analogous to that disclosed in Da-Rocha, et al., *J. Psychopharmacology* (1997) 11(3) 211–218; Smith, et al., *Am. J. Psychiatry* (1998) 155(10) 1339–45; or Le, et al., *Alcohol and Alcoholism* (1996) 31 Suppl. 127–132. Also see, the discussion of the use of the GABA$_A$ receptor ligand 3-(5-methylisoxazol-3-yl)-6-(1-methyl-1,2,3-triazol-4-yl)methyloxy-1,2,4-triazolo [3,4-a]phthalzine in combination with nicotinic agonists, muscarinic agonists, and acetylcholinesterase inhibitors, in PCT International publications Nos. WO 99/47142, WO 99/47171, and WO 99/47131, respectively. Also see in this regard PCT International publication No. WO 99/37303 for its discussion of the use of a class of GABA$_A$ receptor ligands, 1,2,4-triazolo[4,3-b]pyridazines, in combination with SSRIs.

The invention also pertains to methods of inhibiting the binding of benzodiazepine compounds, such as RO15-1788, to the GABA$_A$ receptors which methods involve contacting a compound of the invention with cells expressing GABA$_A$ receptors, wherein the compound is present at a concentration sufficient to inhibit benzodiazepine binding to GABA$_A$ receptors in vitro. This method includes inhibiting the binding of benzodiazepine compounds to GABA$_A$ receptors in vivo, e.g., in a patient given an amount of a compound of Formula I that would be sufficient to inhibit the binding of benzodiazepine compounds to GABA$_A$ receptors in vitro. In one embodiment, such methods are useful in treating benzodiazepine drug overdose. The amount of a compound that would be sufficient to inhibit the binding of a benzodiazepine compound to the GABA$_A$ receptor may be readily determined via a GABA$_A$ receptor binding assay, such as the assay described in Example 5. The GABA$_A$ receptors used to determine in vitro binding may be obtained from a variety of sources, for example from preparations of rat cortex or from cells expressing cloned human GABA$_A$ receptors.

The invention also pertains to methods for altering the signal-transducing activity, particularly the chloride ion conductance, of GABA$_A$ receptors, said method comprising exposing cells expressing such receptors to a therapeutically effective amount of a compound of the invention. This method includes altering the signal-transducing activity of GABA$_A$ receptor s in vivo, e.g., in a patient given an amount of a compound of Formula I that would be sufficient to alter the signal-transducing activity of GABA$_A$ receptors in vitro. The amount of a compound that would be sufficient to alter the signal-transducing activity of GABA$_A$ receptors may be determined via a GABA$_A$ receptor signal transduction assay, such as the assay described in Example 6.

The GABA$_A$ receptor ligands provided by this invention and labeled derivatives thereof are also useful as standards and reagents in determining the ability of a potential pharmaceutical to bind to the GABA$_A$ receptor.

Labeled derivatives the GABA$_A$ receptor ligands provided by this invention are also useful as radiotracers for positron emission tomography (PET) imaging or for single photon emission computerized tomography (SPECT).

More particularly compounds of the invention may be used for demonstrating the presence of GABA$_A$ receptors in cell or tissue samples. This may be done by preparing a plurality of matched cell or tissue samples, at least one of which is prepared as an experiment sample and at least one of which is prepared as a control sample. The experimental sample is prepared by contacting (under conditions that permit binding of RO15-1788 to GABA$_A$ receptors within cell and tissue samples) at least one of the matched cell or tissue samples that has not previously been contacted with any compound or salt of the invention with an experimental solution comprising the detectably-labeled preparation of the selected compound or salt at the first measured molar concentration. The control sample is prepared by in the same manner as the experimental sample and also contains an unlabelled preparation of the same compound or salt of the invention at a greater molar concentration.

The experimental and control samples are then washed to remove unbound detectably-labeled compound. The amount of remaining bound detectably-labeled compound is then measured and the amount of detectably-labeled compound in the experimental and control samples is compared. A comparison that indicates the detection of a greater amount of detectable label in the at least one washed experimental sample than is detected in any of control samples demonstrates the presence of GABA$_A$ receptors in that experimental sample.

The detectably-labeled compound used in this procedure may be labeled with a radioactive label or a directly or indirectly luminescent label. When tissue sections are used in this procedure and the detectably-labeled compound is radiolabeled, the bound, labeled compound may be detected autoradiographically to generate an autoradiogram. The amount of detectable label in an experimental or control sample may be measured by viewing the autoradiograms and comparing the exposure density of the autoradiograms.

As used herein, the term "alkyl" indicates alkyl groups of a designed number of carbon atoms, or from 1 to about 8 carbon atoms. Examples of "alkyl" include methyl, ethyl, propyl, isopropyl, butyl, iso-, sec- and tert-butyl, pentyl, hexyl, heptyl, 3-ethylbutyl, cyclopropyl, cyclobutyl, cyclopentyl, cyclohexyl, cycloheptyl, norbornyl, and the like. When reference is made herein to $C_{1-6}$ alkyl or $C_{1-8}$ alkyl containing one or two double or triple bonds it is understood that at least two carbons are present in the alkyl for one double or triple bond, and at least four carbons for two double or triple bonds.

The term "alkoxy" indicates an alkyl group of indicated number of carbon atoms, or from 1 to about 8 carbon atoms, attached through an oxygen bridge, such as methoxy, ethoxy, propoxy and isopropoxy.

The term "halogen" indicates fluorine, chlorine, bromine, and iodine.

Pharmaceutical Preparations

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl disterate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety, depression, or cognitive impairment a dosage regimen of 1 or 2 times daily is particularly preferred. For the treatment of sleep disorders a single dose that rapidly reaches a therapeutically effective concentration is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

The present invention also pertains to packaged pharmaceutical compositions for treating disorders responsive to GABA$_A$ receptor modulation, e.g., treatment of anxiety, depression, sleep disorders or cognitive impairment by GABA$_A$ receptor modulation. The packaged pharmaceutical compositions include a container holding a therapeutically effective amount of at least one GABA$_A$ receptor modulator as described supra and instructions (e.g., labeling) indicating the contained GABA$_A$ receptor ligand is to be used for treating a disorder responsive to GABA$_A$ receptor modulation in the patient.

Compound Preparation

A general illustration of the preparation of compounds of Formula I in the present invention is given in Scheme 1.

Scheme I

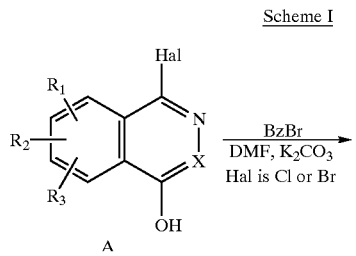

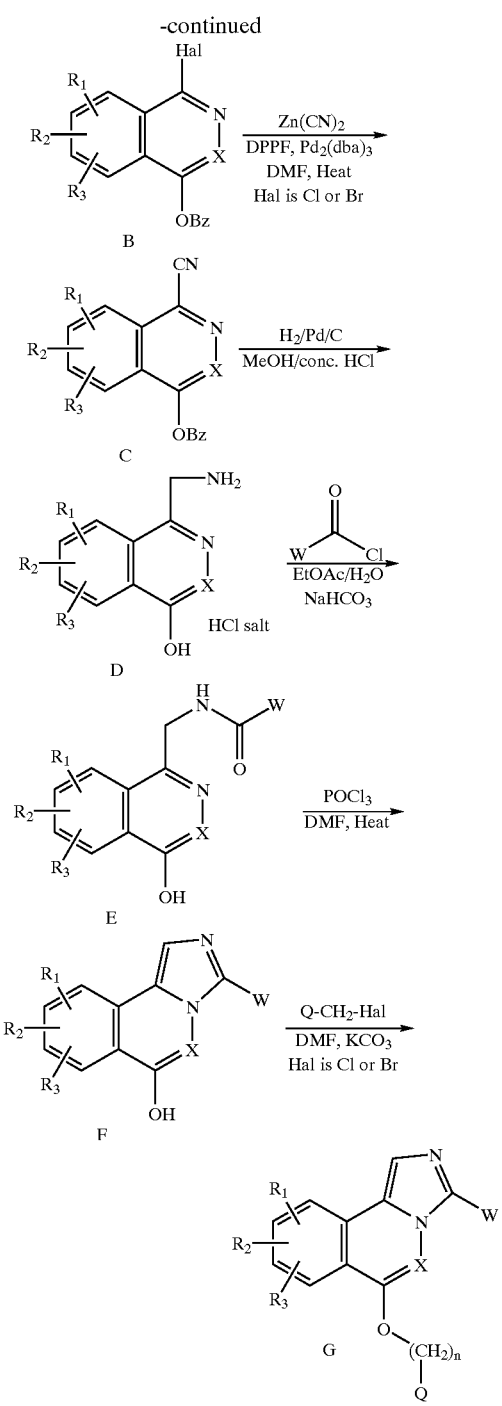

Wherein n, $R_1$, $R_2$, $R_3$, W, Q, and X are as defined above in Formula I.

In Scheme I MeOH is methanol, EtOAc is Ethyl acetate, DPPF is 1,1'-bis(diphenylphosphino)ferrocene, Pd$_2$(dba)$_3$ is tris(dibenzylideneacetone)dipalladium, DMF is dimethylformide, and POCl$_3$ is phosphorus oxychloride. Heat, as used herein, means elevated temperature, such as 40 to 250° C. Those skilled in the art will recognize that in certain instances it will be necessary to utilize different solvents or reagents to achieve some of the above transformations.

The invention is illustrated further by the following examples, which are not to be construed as limiting the invention in scope or spirit to the specific procedures described in them. Those having skill in the art will recognize that the starting materials may be varied and additional steps employed to produce compounds encompassed by the present inventions, as demonstrated by the following examples. Unless otherwise stated starting material and reagents employed in this synthesis are of standard commercial grade. In some cases, protection of certain reactive functionalities may be necessary to achieve some of the above transformations. In general, such need for protecting groups, as well as the conditions necessary to attach and remove such groups, will be apparent to those skilled in the art of organic synthesis.

The starting materials and various intermediates may be obtained from commercial sources, prepared from commercially available organic and/or inorganic reagents and compounds, or prepared using well known synthetic methods.

EXAMPLE 1

Preparation of 3-phenyl-3a-hydroimidazolo[5,1-a]isoquinolin-5-ol

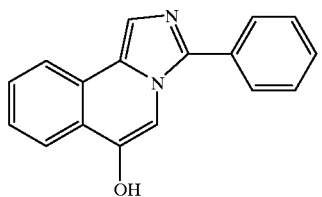

(1) 1-Chloro-4-(phenylmethoxy)isoquinoline

To a mixture of 1-chloroisoquinolin-4-ol (2.33 g, 13 mmol) and potassium carbonate (3 g) in anhydrous DMF (50 mL) is added benyl bromide (1.73 mL, 14.5 mmole) dropwise at room temperature. The resulting solution is stirred at room temperature for 48 hours, and then poured into ice water. The precipitate is collected by filtration and washed with water and hexanes, and dried to give the desired product as a white solid (3.25 g, yield: 93%). m.p. 97–98° C.

(2) 4-(Phenylmethoxy)isoquinolinecarbonitile

A mixture of 1-chloro-4-(phenylmethoxy)isoquinoline (2.26 g, 8.4 mmol), $Zn(CN)_2$ (590 mg), tris(dibenzylideneacetone)dipalladium (219 mg), 1,1'-bis(diphenylphosphino)ferrocene (270 mg) in 100 ml of DMF is heated at 150° C. for 24 h under nitrogen. TLC and LC-MS analysis indicates complete consumption of starting material after 24 h. The mixture is then cooled to 80° C. and gradually diluted with 4:1:4 saturated aq. $NH_4Cl$: concentrated $NH_4OH$:water (200 mL) over 0.5 hours. The slurry is cooled to 0° C. and filtered through celite. The tan solid is collected by filtration, washed and dried to give the titled compound as a tan solid (1.5 g), m.p. 124–125° C.

(3) 1-(Aminomethyl)isoquinolin-4-ol dihydrochloride

A mixture of the product from step 2 (2 g) and 10% Pd on carbon (800 mg) in 50 ml of methanol containing 4 ml of conc. HCl is hydrogenated with a balloon of hydrogen for about half an hour. The mixture is filtered through CELITE and concentrated under vacuum to a solid. Recrystallization from EtOAc and methanol yields the title compound (1.3 g) as a white solid, m.p. 214–216° C (dec).

(4) N-[(4-Hydroxyisoquinolin-1-yl)methyl]benzamide

Benzoyl chloride (0.018 ml) is added dropwise to a stirred mixture of the product from step 3 (20 mg) in a mixture of 2 ml EtOAc and 2 ml of saturated aqueous $NaHCO_3$ solution. After 15 minutes stirring, the organic layer is separated, washed with water, dried and concentrated to a solid. The solid is washed with hexane and dried to yield 20 mg of the title compound as a white solid, m.p. 130–131° C.

(5) 3-Phenyl-3a-hydroimidazo[5,1-a]isoquinolin-5-ol

A mixture of the product from step 4 (20 mg) in 0.02 ml of $POCl_3$ and 5 ml of DMF is stirred at 80° C. for two hours, then cooled and concentrated under vacuum. The residue is treated with EtOAc and washed with aqueous $NaHCO_3$ solution and water. The organic solution is dried over $Na_2SO_4$ and then concentrated to yield the title compound as an off-white solid (0.7 mg), $^1H$ NMR ($CDCl_3$) 7.45 (1H, t), 7.56–7.60 (3H, m), 7.67 (1H, d), 7.72 (1H, t), 7.87 (1H, s), 8.00(1H, s), 8.09 (1H, s) 8.31 (1H, d).

EXAMPLE 2a (6) Synthesis of 3-phenyl-5-(2-pyridylmethoxy)-3a-hydroimidazolo[5,1-a]isoquinoline A mixture of the product from step 5 (1 mmole), 2-picolyl chloride (1.2 mmole) and $K_2CO_3$ (2 mmole) in 2 ml of DMF is heated at 80 for 16 hours. The mixture is added to aqueous $NaHCO_3$ solution and extracted with EtOAc. The organic layer is washed with brine and water, dried, concentrated and purified on a silica gel column to give the titled compound.

EXAMPLE 2b

The following compounds are synthesized using procedures analogous to those described in Scheme I and Examples 1 and 2a.

a) 3-phenyl-5-(2-pyridylmethoxy)-3a-hydroimidazolo[5,1-a]isoquinoline
b) 3-phenyl-5-(3-pyridylmethoxy)-3a-hydroimidazolo[5,1-a]isoquinoline
c) 3-phenyl-5-(4-pyridylmethoxy)-3a-hydroimidazolo[5,1-a]isoquinoline
d) 3-[2'-fluorophenyl]-5-(2-pyridylmethoxy)-3a-hydroimidazolo [5,1-a]isoquinoline
e) 3-[4'-methylphenyl]-5-(2-pyridylmethoxy)-3a-hydroimidazolo [5,1-a]isoquinoline
f) 3-[4'-methoxyphenyl]-5-(2-pyridylmethoxy)-3a-hydroimidazolo [5,1-a]isoquinoline
g) 3-[4'-chlorophenyl]-5-(2-pyridylmethoxy)-3a-hydroimidazolo [5,1-a]isoquinoline
h) 3-[4'-fluorophenyl]-5-(2-pyridylmethoxy)-3a-hydroimidazolo [5,1-a]isoquinoline
i) 3-[4'-trifluoromethylphenyl]-5-(2-pyridylmethoxy)-3a-hydroimidazolo[5,1-a]isoquinoline
j) 3-[2',4'-difluorophenyl]-5-(2-pyridylmethoxy)-3a-hydroimidazolo[5,1-a]isoquinoline
k) 3-[4'-ethylphenyl]-5-(2-pyridylmethoxy)-3a-hydroimidazolo[5,1-a]isoquinoline
l) 3-[4'-ethoxyphenyl]-5-(2-pyridylmethoxy)-3a-hydroimidazolo[5,1-a]isoquinoline
m) 3-[4'-methylphenyl]-5-(imidaolylmethoxy)-3a-hydroimidazolo[5,1-a]isoquinoline
n) 3-phenyl-5-(triazol-4-ylmethoxy)-3a-hydroimidazolo[5,1-a]isoquinoline
o) 3-phenyl-5-(phenylmethoxy)-3a-hydroimidazolo[5,1-a]isoquinoline
p) 3-phenyl-5-(2-thienylmethoxy)-3a-hydroimidazolo[5,1-a]isoquinoline
q) 3-phenyl-5-{(1-Methyl-1H-[1,2,3]triazol-4-yl)methoxy}-imidazo[5,1-a]isoquinoline
r) 3-(4-Fluorophenyl)-5-{(1-Methyl-1H-[1,2,3]triazol-4-yl)methoxy}-imidazo[5,1-a]isoquinoline

EXAMPLE 3
Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

EXAMPLE 4
Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

EXAMPLE 5
Binding Assay

The high affinity and high selectivity of compounds of this invention for the benzodiazepine site of the $GABA_A$ receptor is confirmed using the binding assay described in Thomas and Tallman (J. Bio. Chem. 1981; 156:9838–9842, and J. Neurosci. 1983; 3:433–440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000× g for 20 minutes. The supernatant is decanted, the pellet rehomogenized in the same volume of buffer, and centrifuged again at 20,000× g. The supernatant of this centrifugation step is decanted and the pellet stored at −20° C. overnight. The pellet is then thawed and resuspended in 25 volumes of Buffer A (original wt/vol), centrifuged at 20,000× g and the supernatant decanted. This wash step is repeated once. The pellet is finally resuspended in 50 volumes of Buffer A.

Incubations containi 100 µl of tissue homogenate, 100 µl of radioligand, (0.5 nM $^{3}H$-Ro15-1788 [$^{3}H$-Flumazenil], specific activity 80 Ci/mmol), and test compound or control (see below), and are brought to a total volume of 500 µl with Buffer A. Incubations are carried for 30 min at 4° C. and then rapidly filtered through Whatman GFB filters to separate free and bound ligand. Filters are washed twice with fresh Buffer A and counted in a liquid scintillation counter. Nonspecific binding (control) is determined by displacement of $^{3}H$ R015-1788 with 10 µM Diazepam (Research Biochemicals International, Natick, Mass.). Data were collected in triplicate, averaged, and percent inhibition of total specific binding (Total Specific Binding=Total−Nonspecific) was calculated for each compound.

A competition binding curve is obtained with up to 11 points spanning the compound concentration range from $10^{-12}M$ to $10^{-5}M$ obtained per curve by the method described above for determining percent inhibition. $K_i$ values are calculated according the Cheng-Prussof equation. When tested in this assay compounds of the invention exihibit $K_i$ values of less than 1 uM, preferred compounds of the invention have $K_i$ values of less than 500 nM and more preferred compounds of the invention have $K_i$ values of less than 100 nM.

EXAMPLE 6
Electrophysiology

The following assay is used to determine if a compound of the invention act as an agonist, an antagonist, or an inverse agonist at the benzodiazepine site of the $GABA_A$ receptor.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Electrophysiological recordings are carried out using the two electrode voltage-clamp technique at a membrane holding potential of −70 mV. Xenopus Laevis oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. M82919; human $\beta_3$, GENBANK accession no. Z20136; human $\beta_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 µM GABA is applied.

Compounds are evaluated against a GABA concentration that evokes <10% of the maximal evokable GABA current (e.g. 1 µM-9 µM). Each oocyte is exposed to increasing concentrations of compound in order to evaluate a concentration/effect relationship. Compound efficacy is calculated as a percent-change in current amplitude: 100*((Ic/I)-1), where Ic is the GABA evoked current amplitude observed in the presence of test compound and I is the GABA evoked current amplitude observed in the absence of the test compound.

Specificity of a compound for the benzodiazepine site is determined following completion of a concentration/effect curve. After washing the oocyte sufficiently to remove previously applied compound, the oocyte is exposed to GABA+1 μM RO15-1788, followed by exposure to GABA+1 μM RO15-1788+test compound. Percent change due to addition of compound is calculated as described above. Any percent change observed in the presence of RO15-1788 is subtracted from the percent changes in current amplitude observed in the absence of 1 μM RO15-1788. These net values are used for the calculation of average efficacy and $EC_{50}$ values by standard methods. To evaluate average efficacy and $EC_{50}$ values, the concentration/effect data are averaged across cells and fit to the logistic equation.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula

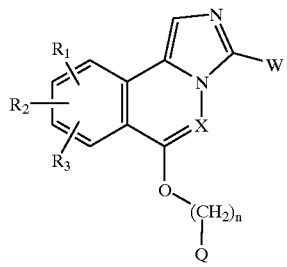

or a pharmaceutically acceptable salt thereof, wherein:

n is 1, 2, 3, or 4, $R_1$, $R_2$, and $R_3$ are the same or different and represent:
  i) hydrogen, halogen, hydroxy,
  ii) $R_a$ wherein $R_a$ is —O($C_{1-8}$ alkyl), —$NO_2$, —CN, —$SO_2NH_2$, —$SO_2NH(C_{1-8}$ alkyl), —$SO_2N(C_{1-8}$ alkyl)($C_{1-8}$ alkyl), amino, —NH($C_{1-8}$ alkyl), —N($C_{1-8}$ alkyl) ($C_{1-8}$ alkyl), —NHCO($C_{1-8}$ alkyl), —N($C_{1-8}$ alkyl)CO($C_{1-8}$ alkyl), —NHCO$_2$($C_{1-8}$ alkyl) —N($C_{1-8}$ alkyl)CO$_2$($C_{1-8}$ alkyl), —NHSO$_2$($C_{1-8}$ alkyl), —CONH$_2$, —CONH($C_{1-8}$ alkyl), —CON($C_{1-8}$ alkyl) ($C_{1-8}$ alkyl), —CO$_2$($C_{1-8}$ alkyl), —S($C_{1-8}$ alkyl), —SO ($C_{1-8}$ alkyl), or —SO$_2$($C_{1-8}$ alkyl),
    wherein each $C_{1-8}$ alkyl independently is straight, branched or cyclic, contains zero, one or two double or triple bonds, and is optionally substituted with one or more of hydroxy, oxo, halogen, amino, or $C_{1-8}$ alkoxy,
  or $R_a$ is $C_{1-8}$ alkyl, which is straight, branched or cyclic, contains zero, one or two double or triple bonds, and is unsubstituted or substituted with one or more of
    a) hydroxy, b) oxo, c) halogen, e) —O($C_{1-8}$ alkyl),
    f) —NR$_4$R$_5$ wherein
      R$_4$ and R$_5$ are independently selected from hydrogen and $C_{1-8}$ alkyl, or
      R$_4$ and R$_5$ may be joined together to form a monocyclic or bicyclic ring, each of which may contain one or more double bonds, or where one or more of the ring members is carbonyl, O, S, SO, SO$_2$ or N—R$_6$, wherein R$_6$ is hydrogen, $C_{1-6}$ alkyl, $C_{1-6}$ alkyl-Ar$_2$, wherein Ar$_2$ is attached to $C_{1-6}$ alkyl at any position and is optionally substituted with one or two groups, R$_b$ and R$_c$, wherein R$_b$ and R$_c$ independently carry the definition of R$_a$, or
  g) —CONR$_7$R$_8$, or —CO$_2$R$_7$ wherein each R$_7$ and R$_8$ is independently hydrogen or $C_{1-6}$ alkyl, iii) Ar$_1$,
  wherein Ar$_1$ is phenyl, pyridyl, pyrazlnyl, pyrimidinyl, imidazolyl, furanyl, thiazolyl, isothiazolyl, isoxazolyl, oxadiazolyl, triazolyl, tetrazolyl, or pyrazolyl, each of which is unsubstituted or substituted with hydrogen, halogen, hydroxy, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl) ($C_{1-8}$ alkyl) amino, —NH($C_{1-8}$ alkyl), —N($C_{1-8}$ alkyl) ($C_{1-8}$ alkyl), —NHCO($C_{1-8}$ alkyl), —N($C_{1-8}$ alkyl) CO($C_{1-8}$ alkyl), —NHCO$_2$ ($C_{1-8}$ alkyl), —N($C_{1-8}$ alkyl)CO$_2$($C_{1-8}$ alkyl), —NHSO$_2$($C_{1-8}$ alkyl), —CONH$_2$, —CONH($C_{1-8}$ alkyl), —CON($C_{1-8}$ alkyl) ($C_{1-8}$ alkyl), —CO$_2$($C_{1-8}$ alkyl), —S($C_{1-8}$ alkyl), —SO($C_{1-8}$ alkyl), or —SO$_2$ ($C_{1-8}$ alkyl), —CON$_7$R$_8$, or —CO$_2$R$_7$ (wherein each R$_7$ and R$_8$ is independently hydrogen or $C_1$-$C_6$ alkyl)
  wherein each $C_{1-8}$ alkyl independently is straight, branched or cyclic, contains zero, one or two double or triple bonds, and is optionally substituted with one or more of hydroxy, oxo, halogen, amino, or $C_{1-8}$ alkoxy;

X is CH, or CR$_d$, wherein R$_d$ carries the same definition as R$_a$;

W is phenyl, unsubstituted or substituted with one or more of hydrogen, halogen, hydroxy, alkoxy, R$_x$ where R$_x$ carries the same definition as R$_a$, or Ar$_3$ wherein Ar$_3$ carries the same definition as Ar$_1$; and Q is phenyl, thienyl, benzothienyl, pyridyl, isoquinolyl, quinolyl, pyrazinyl, pyrimidinyl, imidazolyl, benzoimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, benzopyrazolyl, each of which is unsubstituted or substituted with one or more of:
  hydrogen, halogen, hydroxy, alkoxy, R$_y$ where R$_y$ carries the same definition as R$_a$, or Ar$_4$ wherein Ar$_4$ carries the same definition as Ar$_1$.

2. A compound or salt according to claim 1 wherein X is CH.

3. A compound or salt according to claim 1 of the formula

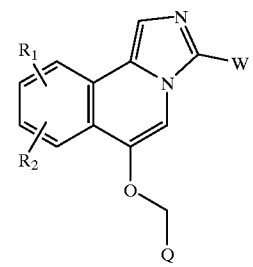

wherein W, Q, $R_1$ and $R_2$ are as defined in claim 1.

4. A compound or salt according to claim 1 of the formula

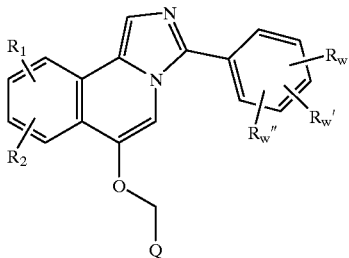

wherein $R_w$, $R_w'$, and $R_w''$ independently represent hydrogen, halogen, hydroxy, or $R_z$ wherein $R_z$ carries the same definition as $R_a$ in claim 1.

5. A compound of the formula

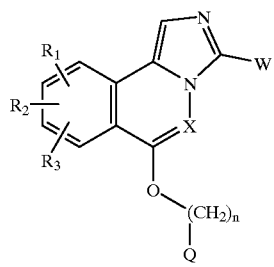

or a pharmaceutically acceptable salt thereof, wherein:
n is 1, 2, 3, or 4,
$R_1$, $R_2$ and $R_3$ are independently selected from hydrogen, halogen, hydroxy, $C_{1-8}$ alkyl, —O($C_{1-8}$ alkyl), —NO$_2$, —CN, amino, —NH($C_{1-8}$ alkyl), and —N($C_{1-8}$ alkyl) ($C_{1-8}$ alkyl);
X is CH or C($C_{1-6}$ alkyl);
W is phenyl, unsubstituted or substituted with one to three groups independently selected from halogen, hydroxy, $C_{1-8}$alkyl, —O($C_{1-8}$ alkyl), —NO$_2$, —CN, amino, —NH($C_{1-8}$ alkyl), and —N($C_{1-8}$ alkyl) ($C_{1-8}$ alkyl); and is phenyl, thienyl, pyridyl, pyrazinyl, pyrimidinyl, imidazolyl, furanyl, thiazolyl, pyrrolyl, triazolyl, or pyrazolyl;
each of which is unsubstituted or substituted with one to three groups independently selected from halogen, hydroxy, $C_{1-8}$ alkyl, —O($C_{1-8}$ alkyl), —NO$_2$, —CN, amino, —NH($C_{1-8}$ alkyl) and —N($C_{1-8}$ alkyl) ($C_{1-8}$ alkyl).

6. A compound or salt according to claim 5, wherein X is CH and $R_1$, $R_2$, $R_3$, W, n, and Q are as defined in claim 5.

7. A compound or salt according to claim 5 of the formula

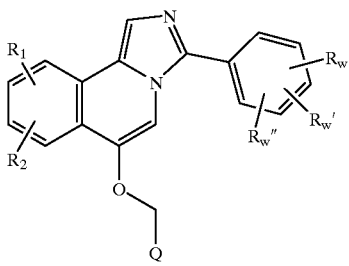

wherein $R_1$, $R_2$, and Q are as defined in claim 5 and $R_w$, $R_w'$, and $R_w''$ are independently chosen from hydrogen, halogen, hydroxy, $C_{1-4}$alkyl, —O($C_{1-4}$ alkyl), —NO$_2$, —CN, -amino, —NH($C_{1-4}$ alkyl), and —N($C_{1-4}$ alkyl) ($C_{1-4}$ alkyl).

8. A compound according to claim 1, which is: 3-phenyl-5-(2-pyridylmethoxy)-3a-hydroimidazolo[5,1-a]isoquinoline, or a pharmaceutically acceptable salt thereof.

9. A compound according to claim 1, which is: 3-phenyl-5-(3-pyridylmethoxy)-3a-hydroimidazolo[5,1-a]isoquinoline, or a pharmaceutically acceptable salt thereof.

10. A compound according to claim 1, which is: 3-phenyl-5-(4-pyridylmethoxy)-3a-hydroimidazolo[5,1-a]isoquinoline, or a pharmaceutically acceptable salt thereof.

11. A compound according to claim 1, which is: 3-[2'-fluorophenyl]-5-(2-pyridylmethoxy)-3a-hydroimidazolo[5,1-a]isoquinoline, or a pharmaceutically acceptable salt thereof.

12. A compound according to claim 1, which is: 3-[4'-methylphenyl]-5-(2-pyridylmethoxy)-3a-hydroimidazolo[5,1-a]isoquinoline, or a pharmaceutically acceptable salt thereof.

13. A compound according to claim 1, which is: 3-[4'-methoxyphenyl]-5-(2-pyridylmethoxy)-3a-hydroimidazolo[5,1-a]isoquinoline, or a pharmaceutically acceptable salt thereof.

14. A compound according to claim 1, which is: 3-[4'-chlorophenyl]-5-(2-pyridylmethoxy)-3a-hydroimidazolo[5,1-a]isoquinoline, or a pharmaceutically acceptable salt thereof.

15. A compound according to claim 1, which is: 3-[4'-fluorophenyl]-5-(2-pyridylmethoxy)-3a-hydroimidazolo[5,1-a]isoquinoline, or a pharmaceutically acceptable salt thereof.

16. A compound according to claim 1, which is: 3-[4'-trifluoromethylphenyl]-5-(2-pyridylmethoxy)-3a-hydroimidazolo[5,1-a]isoquinoline, or a pharmaceutically acceptable salt thereof.

17. A compound according to claim 1, which is: 3-[2',4'-difluorophenyl]-5-(2-pyridylmethoxy)-3a-hydroimidazolo[5,1-a]isoquinoline, or a pharmaceutically acceptable salt thereof.

18. A compound according to claim 1, which is: 3-[4'-ethylphenyl]-5-(2-pyridylmethoxy)-3a-hydroimidazolo[5,1-a]isoquinoline, or a pharmaceutically acceptable salt thereof.

19. A compound according to claim 1, which is: 3-[4'-ethoxyphenyl]-5-(2-pyridylmethoxy)-3a-hydroimidazolo[5,1-a]isoquinoline, or a pharmaceutically acceptable salt thereof.

20. A compound according to claim 1, which is: 3-[4'-methylphenyl]-5-(imidaz-2-ylmethoxy)-3a-hydroimidazolo[5,1-a]isoquinoline, or a pharmaceutically acceptable salt thereof.

21. A compound according to claim 1, which is: 3-phenyl-5-(triazol-4-ylmethoxy)-3a-hydroimidazolo[5,1-a]isoquinoline, or a pharmaceutically acceptable salt thereof.

22. A compound according to claim 1, which is: 3-phenyl-5-(phenylmethoxy)-3a-hydroimidazolo[5,1-a]isoquinoline, or a pharmaceutically acceptable salt thereof.

23. A compound according to claim 1, which is: 3-phenyl-5-(2-thienylmethoxy)-3a-hydroimidazolo[5,1-a]isoquinoline, or a pharmaceutically acceptable salt thereof.

24. A compound according to claim 1, which is 3-phenyl-5-{(1-Methyl-1H-[1,2,3]triazol-4-yl)methoxy}-imidazo[5,1-a]isoquinoline, or a pharmaceutically acceptable salt thereof.

25. A compound according to claim 1, which is 3-(4-Fluorophenyl)-5-{(1-Methyl-1H-[1,2,3]triazol-4-yl)methoxy}-imidazo[5,1-a]isoquinoline, or a pharmaceutically acceptable salt thereof.

26. A compound of the formula

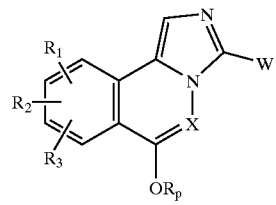

or a pharmaceutically acceptable salt thereof wherein $R_1$, $R_2$, and $R_3$ are the same or different and represent:
i) hydrogen, halogen, hydroxy,
ii) $R_a$ wherein $R_a$ is —O($C_{1-8}$ alkyl), —$NO_2$, —CN, —$SO_2NH_2$, —$SO_2NH(C_{1-8}$ alkyl), —$SO_2N(C_{1-8}$ alkyl)($C_{1-8}$ alkyl), amino, —NH($C_{1-8}$ alkyl), —N($C_{1-8}$ alkyl) ($C_{1-8}$ alkyl), —NHCO($C_{1-8}$ alkyl), —N($C_{1-8}$ alkyl)CO($C_{1-8}$ alkyl), —$NHCO_2$ ($C_{1-8}$ alkyl) —($C_{1-8}$ alkyl), $CO_2(C_{1-8}$ alkyl), —$NHSO_2(C_{1-8}$ alkyl), —$CONH_2$, —CONH($C_{1-8}$ alkyl), —CON($C_{1-8}$ alkyl) ($C_{1-8}$ alkyl), —$CO_2(C_{1-8}$ alkyl), —S($C_{1-8}$ alkyl), —SO ($C_{1-8}$ alkyl), or —$SO_2(c_{1-8}$ alkyl),
wherein each $C_{1-8}$ alkyl independently is straight, branched or cyclic, contains zero, one or two double or triple bonds, and is optionally substituted with one or more of hydroxy, oxo, halogen, amino, or $C_{1-8}$ alkoxy,
or $R_a$ is $C_{1-8}$ alkyl, which is straight, branched or cyclic, contains zero, one or two double or triple bonds, and is unsubstituted or substituted with one or more of
hydroxy,
oxo,
halogen,
—O($C_{1-8}$ alkyl),
—$NR_4R_5$ wherein
$R_4$ and $R_5$ are independently selected from hydrogen and $C_{1-8}$ alkyl, or
$R_4$ and $R_5$ may be joined together to form a monocyclic or bicyclic ring, each of which may contain one or more double bonds, or
where one or more ring members is carbonyl, O, S, SO, $SO_2$ or N—$R_6$,
wherein $R_6$ is hydrogen, $C_{1-6}$ alkyl, $C_{1-6}$ alkyl-$Ar_2$, wherein $Ar_2$ is attached to $C_{1-6}$ alkyl at any position and is optionally substituted with one or two groups, $R_b$ and $R_c$, wherein $R_b$ and $R_c$ independently carry the definition of $R_a$, or
—$CONR_7R_8$, or —$CO_2R_7$ wherein each $R_7$ and $R_8$ is independently hydrogen of $C_{1-8}$ alkyl,
iii) $Ar_1$,
wherein $Ar_1$ is phenyl, pyridyl, pyrazinyl, pyrimidyl, imidazolyl, furanyl, thiazolyl, isothiazolyl, isoxazolyl, oxadiazolyl, triazolyl, tetrazolyl, or pyrazolyl, each of which is unsubstituted or substituted with
hydrogen, halogen, hydroxy, $C_{1-8}$ alkyl, —O($C_{1-8}$ alkyl), —$NO_2$, —CN, —$SO_2NH_2$, —$SO_2NH(C_{1-8}$ alkyl), —$SO_2N(C_{1-8}$ alkyl) ($C_{1-8}$ alkyl), amino, —NH($C_{1-8}$ alkyl), —N($C_{1-8}$ alkyl) ($C_{1-8}$ alkyl), —NHCO($C_{1-8}$ alkyl), —N($C_{1-8}$ alkyl)CO($C_{1-8}$ alkyl), —$NHCO_2(C_{1-8}$ alkyl), —N($C_{1-8}$ alkyl)$CO_2(C_{1-8}$ alkyl), —$NHSO_2$ ($C_{1-8}$ alkyl), —$CONH_2$, —CONH($C_{1-8}$ alkyl), —CON ($C_{1-8}$ alkyl) ($C_{1-8}$ alkyl), —$CO_2(C_{1-8}$ alkyl), —S($C_{1-8}$ alkyl, —SO($C_{1-8}$ alkyl), or —$SO_2(C_{1-8}$ alkyl),
wherein each $C_{1-8}$ alkyl independently is straight, branched or cyclic, contains zero, one or two double or triple bonds, and is optionally substituted with one or more of hydroxy, oxo, halogen, amino, or $C_{1-8}$ alkoxy;
—$CONR_7R_8$, or —$CO_2R_7$ wherein each $R_7$ and $R_8$ is independently hydrogen or $C_1$–$C_6$ alkyl;
X is $CR_d$, wherein $R_d$ carries the same definition as $R_a$;
W is phenyl, unsubstituted or substituted with one or more of: hydrogen, halogen, hydroxy, alkoxy, $R_x$ where $R_x$ carries the same definition as $R_a$, or $Ar_3$ wherein $Ar_3$ carries the same definition as $Ar_1$; and
$R_p$ hydrogen, $C_1$–$C_6$ alkyl, or phenyl ($C_1$–$C_6$) alkyl.

* * * * *